US007354417B1

(12) United States Patent
Levin et al.

(10) Patent No.: US 7,354,417 B1
(45) Date of Patent: Apr. 8, 2008

(54) METHODS AND APPARATUS FOR MEASURING THE VOLUME OF FLUID IN THE PERITONEAL CAVITY

(76) Inventors: Nathan W. Levin, 200 E. 89th St., Apartment 17B, New York, NY (US) 10128; Daniel Schneditz, Pfeifferhofweg 66, Graz (AT) 8045; Fansan Zhu, 43-73 Union St., Apartment 4D, Flushing, NY (US) 11355

( * ) Notice: Subject to any disclaimer, the term of this patent is extended or adjusted under 35 U.S.C. 154(b) by 603 days.

(21) Appl. No.: 10/089,831

(22) PCT Filed: Sep. 29, 2000

(86) PCT No.: PCT/US00/27048

§ 371 (c)(1),
(2), (4) Date: Apr. 4, 2002

(87) PCT Pub. No.: WO01/24847

PCT Pub. Date: Apr. 12, 2001

Related U.S. Application Data

(60) Provisional application No. 60/157,785, filed on Oct. 5, 1999.

(51) Int. Cl.
*A61M 1/00* (2006.01)

(52) U.S. Cl. ........................................................ 604/29

(58) Field of Classification Search ............ 604/27-31; 600/382, 384, 547
See application file for complete search history.

(56) References Cited

U.S. PATENT DOCUMENTS 3,871,359 A * 3/1975 Pacela ........................ 600/547
4,008,712 A 2/1977 Nyboer
4,059,169 A * 11/1977 Hagen ........................ 600/481

(Continued)

FOREIGN PATENT DOCUMENTS

WO WO 97/01303 1/1997

OTHER PUBLICATIONS

Rallison et al., "Errors in estimating peritoneal fluid by bioelectrical impedance analysis and total body electrical conductivity," *Journal of the American College of Nutrition*, 12:66-72, 1993.

(Continued)

*Primary Examiner*—Kevin C. Sirmons
*Assistant Examiner*—Catherine N. Witczak
(74) *Attorney, Agent, or Firm*—Maurice M. Klee

(57) ABSTRACT

Methods and apparatus for determining peritoneal cavity fluid volume include four groups of two electrodes applied to a subject's skin. Measuring electrodes (MLL, MRL) are applied to the subject's loins, measuring electrodes (MLB, MRB) are applied to the subject's buttocks, and upper and lower current-providing electrodes (IRU, ILU, IRL, ILL) are applied to the subject's left and right sides distal from the measuring electrodes (MLL, MRL, MLB, MRB). The resistance between left measuring electrodes (MLL, MLB) is measured and the resistance between right measuring electrodes (MRL, MRB) is measured while current is applied between the upper and lower current-providing electrodes. By averaging resistance values, in combination with a calibration procedure, measurements of peritoneal cavity fluid volume are obtained. The measurement techniques can be used in continuous flow peritoneal dialysis to control or adjust dialysis parameters based on peritoneal cavity fluid.

40 Claims, 6 Drawing Sheets

MRL
MLL
MRB
MLB
V
PC
V
IRU
ILU
I
IRL
ILL

U.S. PATENT DOCUMENTS

| | | | | |
|---|---|---|---|---|
| 4,450,527 | A | | 5/1984 | Sramek |
| 4,793,362 | A | | 12/1988 | Tedner |
| 4,911,175 | A | | 3/1990 | Shizgal |
| 4,947,862 | A | | 8/1990 | Kelly |
| 5,643,201 | A | * | 7/1997 | Peabody et al. ............. 604/31 |
| 5,735,284 | A | | 4/1998 | Tsoglin et al. |
| 5,788,643 | A | | 8/1998 | Feldman |
| 5,791,349 | A | | 8/1998 | Shmulewitz |

OTHER PUBLICATIONS

Schneditz et al., "Kinetics of fluid removal during hemodialysis (HD) measured by segmental bioimpendance," *J Amer Soc Nephrol.,* 1997, A1334.

Zhu et al., "Continuous measurement of segmental and whole body bio-impendance," *Proc IEEE EMBS,* 1997, 19:2086-2088.

Zhu et al., " Estimation of trunk extracellular volume by bioimpedance," *Proc IEEE EMBS,* 1998, 20:3104-3107.

Zhu et al., "Dynamics of segmental extracellular volumes during changes in body position by bioimpendance analysis," *J. Appl. Physiol,* 1998, 85:497-504.

Zhu et al., "Validation of changes in extracellular volume measured during hemodialysis using a segmental bioimpendance technique," *ASAIO Journal,* 1998, 44:M541-M545.

Zhu et al., "Low central fraction of extracellular volume (Fc) relates to hypotension during hemodialysis (HD) and ultrafiltration (UF)," *J Amer Soc Nephrol.,* 1998, A0966.

Zhu et al., "Changes in segmental extracellular volume (ECV) and Blood volume (BV) during ultrafiltration (UF)," *J Amer Soc Nephrol.,* 1998, A0967.

Zhu et al., "Changes in extracellular volume during hemodialysis and ultrafiltration estimated from sum of segmental bioimpedance analysis," *ASLAO Abstracts,* Annual Conference, New York, Apr. 23-25, 1998, 73A.

Zhu et al., "Effect of body position on estimation of extracellular volume (ECV) using whole body and segmental bioimpendance analysis," *ASIAO Abstracts,* Annual Conference, New York, Apr. 23-25, 1998, 85A.

Zhu et al., "Changes in body extracellular fluid during periotoneal dialysis measured by segmental bioimpendance analysis," Proceedings of the 15th International Congress of Nephrology, Buenos Aires, Argentina, May 2-6, 1999.

* cited by examiner

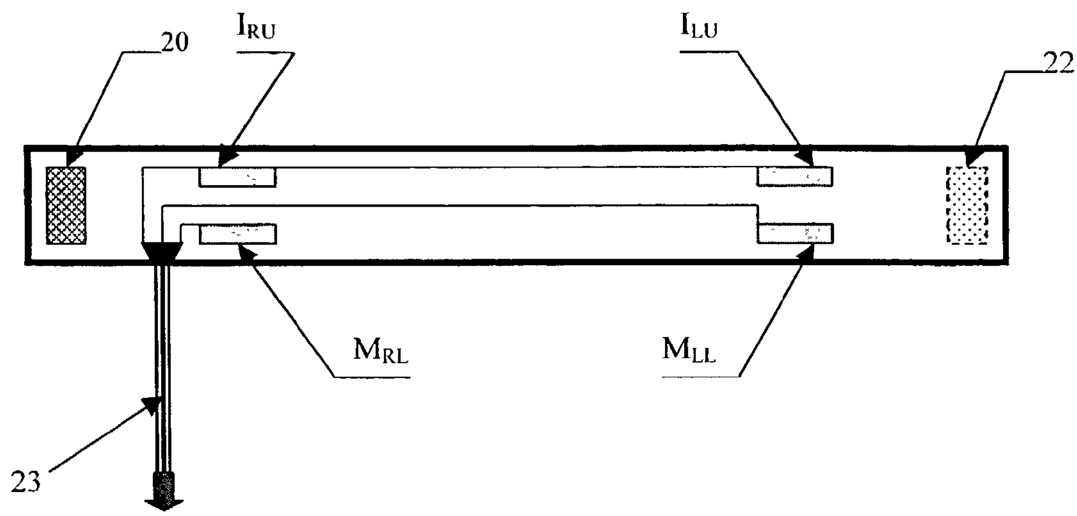
FIG. 6A
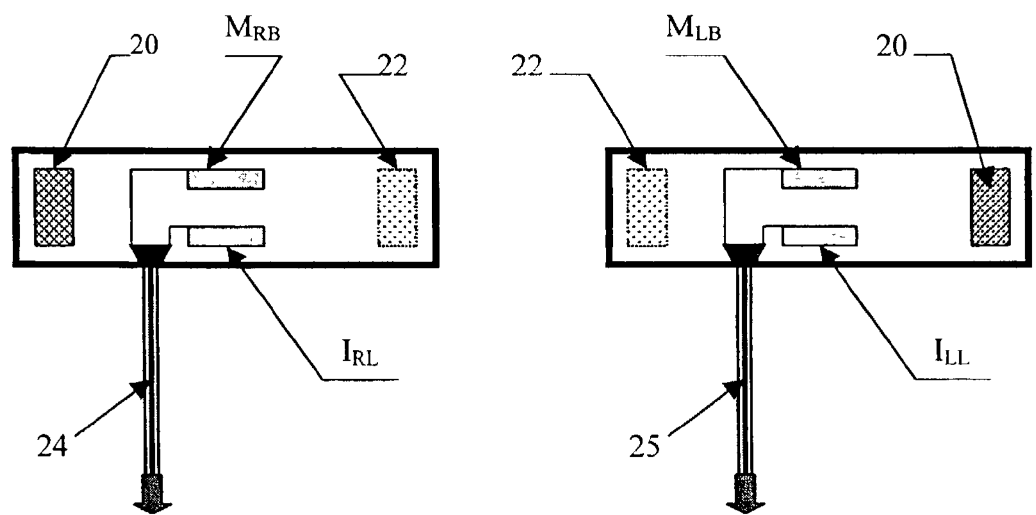
FIG. 6B
FIG. 6C

METHODS AND APPARATUS FOR MEASURING THE VOLUME OF FLUID IN THE PERITONEAL CAVITY

CROSS REFERENCE TO RELATED APPLICATIONS

This application is the U.S. national phase under 35 USC §371 of International Application No. PCT/US00/27048 filed Sep. 29, 2000, which was published in English under PCT Article 21(2) on Apr. 12, 2001 as International Publication No. WO 01/24847. This application claims the benefit under 35 USC §119(e) of U.S. Provisional Application No. 60/157,785 filed Oct. 5, 1999.

FIELD OF THE INVENTION

This invention relates to peritoneal dialysis and, in particular, to the measurement of the volume of fluid in the peritoneal cavity during such dialysis.

BACKGROUND OF THE INVENTION

Peritoneal dialysis involves introducing dialysis fluid into the peritoneal cavity of a subject. Conventionally, the dialysis fluid is introduced and removed batch wise (i.e., in cycles) to facilitate control of the dialysis process, i.e., to allow measurements to be performed on the dialysate as the procedure progresses, e.g., measurements of the volume of the dialysate introduced and removed from the subject.

It has been recognized in the art for some time that continuous flow of dialysate to and from the subject would improve the efficiency of peritoneal dialysis. For example, where a batch wise procedure typically passes 2 liters of dialysate through the peritoneal cavity in an hour, a continuous process will pass 18 liters in the same period of time. This passage of large volumes of dialysate means that substantially greater amounts of uremic toxins can be removed using the continuous approach as compared to the batch wise approach.

The continuous approach, however, runs the risk of a significant accumulation of fluid in the peritoneal cavity through ultrafiltration of the subject's bodily fluids into the dialysate. Alternatively, high levels of fluid can be absorbed into the subject's tissues, which is also potentially dangerous. Prior to the present invention, the only way to address these risks was to periodically stop the process and determine the amount of fluid in the peritoneal cavity by draining the fluid and measuring its volume. This, of course, defeats the goal of having a continuous process and makes the process less acceptable to the subject.

Prior workers in the art have considered using so called whole-body bioimpedance measurements to estimate the volume of fluid in the peritoneal cavity during batch wise peritoneal dialysis. See Rallison et al., "Errors in estimating peritoneal fluid by bioelectrical impedance analysis and total body electrical conductivity," *Journal of the American College of Nutrition,* 12:66-72, 1993. These workers concluded that this measurement technique did not provide a reliable measurement of changes in fluid volume in the peritoneal cavity.

Significantly, this prior unsuccessful work did not involve continuous peritoneal dialysis where the need for fluid volume measurement is more critical than in a batch wise setting. In particular, in continuous peritoneal dialysis, one needs at least periodic and, preferably, a continuous measurement of changes in the volume of fluid in the peritoneal cavity to ensure the safety of the subject. Moreover, for the same reason, the measurement needs to be reliable.

SUMMARY OF THE INVENTION

In view of the foregoing, it is an object of the invention to provide improved methods and apparatus for determining the volume of fluid in the peritoneal cavity of a subject, i.e., a human or an animal. It is a further object of the invention to employ such methods and apparatus in a continuous peritoneal dialysis procedure. It is an additional object of the invention to employ such methods and apparatus in connection with tests of peritoneal function in subjects undergoing dialysis, e.g., in conjunction with a peritoneal equilibration test (PET).

To achieve these and other objects, the invention provides a method for determining the volume of fluid in the peritoneal cavity of a subject comprising:

(a) placing measuring electrodes $M_{LL}$ and $M_{RL}$ on the loins of the subject, $M_{LL}$ being placed on the left loin and $M_{RL}$ being placed on the right loin, $M_{LL}$ and $M_{RL}$ defining a loin plane;

(b) placing measuring electrodes $M_{LB}$ and $M_{RB}$ on the buttocks of the subject, $M_{LB}$ being placed on the left buttock and $M_{RB}$ being placed on the right buttock, $M_{LB}$ and $M_{RB}$ defining a buttock plane;

(c) placing upper current-providing electrodes $I_{LU}$ and $I_{RU}$ on the subject, $I_{LU}$ being outboard of measuring electrode $M_{LL}$ and $I_{RU}$ being outboard of measuring electrode $M_{RL}$;

(d) placing lower current-providing electrodes $I_{RL}$ and $I_{LL}$ on the subject, $I_{RL}$ being outboard of measuring electrode $M_{RB}$ and $I_{LL}$ being outboard of measuring electrode $M_{LB}$;

(e) connecting upper current-providing electrode $I_{LU}$ to upper current-providing electrode $I_{RU}$;

(f) connecting lower current-providing electrode $I_{LL}$ to lower current-providing electrode $I_{RL}$;

(g) applying current I between the connected upper current-providing electrodes and the connected lower current-providing electrodes;

(h) measuring the voltage $\Phi_L$ between $M_{LL}$ and $M_{LB}$ while current I is applied;

(i) measuring the voltage $\Phi_R$ between $M_{RL}$ and $M_{RB}$ while current I is applied; and (j) determining the volume V of fluid in the peritoneal cavity based on the equation:

$$V=(K_P/\sigma)\cdot(L_P^2/R) \qquad \text{Eq. (1)}$$

where:

(1) $K_P$ is a subject-specific calibration constant;

(2) $\sigma$ is the conductivity of the fluid in the peritoneal cavity;

(3) $L_P$ is the distance between the loin plane and the buttock plane; and (4) R is the average of $R_L$ and $R_R$, where $$R_L=\Phi_L/I, \text{ and}$$

$$R_R=\Phi_R/I.$$

In certain embodiments of the invention, $K_P$ is determined by:

(i) performing steps (g), (h), and (i) before the introduction of a predetermined volume $V_C$ of dialysis fluid into the subject's peritoneal cavity to obtain $\Phi_{LB}$ and $\Phi_{RB}$, said dialysis fluid having a conductivity $\sigma_C$;

(ii) performing steps (g), (h), and (i) after the introduction of a predetermined volume $V_C$ of dialysis fluid into the subject's peritoneal cavity to obtain $\Phi_{LA}$ and $\Phi_{RA}$; and (iii) determining $K_P$ from the equation:

$$K_P=(\sigma_C)\cdot(V_C/L_P^2)\cdot(R_B R_A)/(R_B-R_A) \quad \text{Eq. (2)}$$

where $$R_B=(\Phi_{LB}+\Phi_{RB})/(2I), \text{ and}$$

$$R_A=(\Phi_{LA}+\Phi_{RA})/(2I).$$

In other embodiments, $K_P$ is determined by:

(i) introducing dialysis fluid into the subject's peritoneal cavity;

(ii) performing steps (g), (h), and (i) to obtain $\Phi_{LB}$ and $\Phi_{RB}$;

(iii) removing fluid from the subject's peritoneal cavity;

(iv) performing steps (g), (h), and (i) to obtain $\Phi_{LA}$ and $\Phi_{RA}$; and (v) determining $K_P$ from the equation:

$$K_P=(\sigma_C)\cdot(V_C/L_P^2)\cdot(R_B R_A)/(R_A-R_B) \quad \text{Eq. (3)}$$

where $R_B=(\Phi_{LB}+\Phi_{RB})/(2I)$, $R_A=(\Phi_{LA}+\Phi_{RA})/(2I)$, and $V_C$ and $\sigma_C$ are, respectively, the volume and conductivity of the fluid removed in step (iii).

In accordance with others of its aspects, the invention provides a method of controlling a peritoneal dialysis procedure comprising:

(A) continuously flowing dialysis fluid through a subject's peritoneal cavity, said flowing of dialysis fluid being capable of causing the accumulation of ultrafiltrate from the subject in the peritoneal cavity;

(B) determining the volume of fluid in the peritoneal cavity while step (A) is being performed by a bioimpedance measurement directed at the peritoneal cavity; and (C) controlling step (A) based on the volume of fluid in the peritoneal cavity determined in step (B).

Preferably, step (B) is performed by using the above-described bioimpedance method for determining the volume of fluid in the peritoneal cavity of the subject.

In accordance with still further of its aspects, the invention provides apparatus for practicing the above methods, including suitably programmed computers, e.g., personal computers, for performing the computation aspects of the invention.

As used herein and illustrated in FIG. 1, the term "loin" means the region of a subject's body at approximately the level of the bottom of the rib cage, plus or minus 5-10 centimeters. The loin region includes the subject's front, back, and sides at this level.

As used herein and illustrated in FIG. 1, the term "buttock" means the rounded part of the back of the hips and the uppermost part of the thighs.

The terms "upper" and "lower" are used in an electrical sense relative to the subject's peritoneal cavity irrespective of the actual orientation of the subject. Thus, the passage of current from the upper electrodes to the lower electrodes causes at least some current to flow through the subject's peritoneal cavity from its thoracic end to its pelvic end irrespective of whether the subject is standing, sitting, or laying down. For a standing subject with his/her arms above his/her head, the gravity-based definitions of "upper" and "lower" and the electrical-based definitions are the same.

BRIEF DESCRIPTION OF THE DRAWINGS

FIG. 6 is a schematic diagram illustrating common supports that can be used for (1) the upper current-providing electrodes and the loin measuring electrodes (FIG. 6A) and (2) the lower current-providing electrodes and buttock measuring electrodes (FIGS. 6B and 6C).

The foregoing drawings, which are incorporated in and constitute part of the specification, illustrate various embodiments of the invention, and together with the description, serve to explain the principles of the invention. It is to be understood, of course, that both the drawings and the description are explanatory only and are not restrictive of the invention.

DESCRIPTION OF THE PREFERRED EMBODIMENTS

Figure 1:
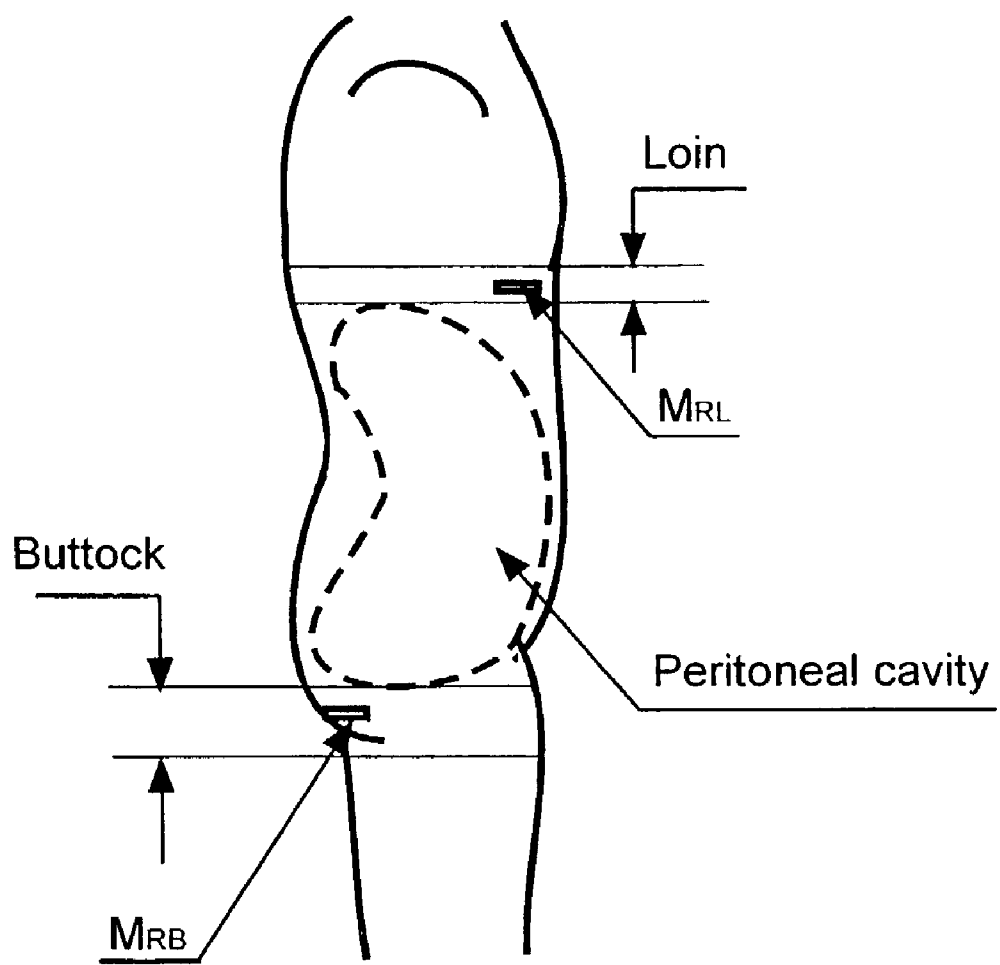
FIG. 1 is a schematic diagram illustrating the meaning of the terms "loin" and "buttock" as used in the specification and claims.
Figure 2:
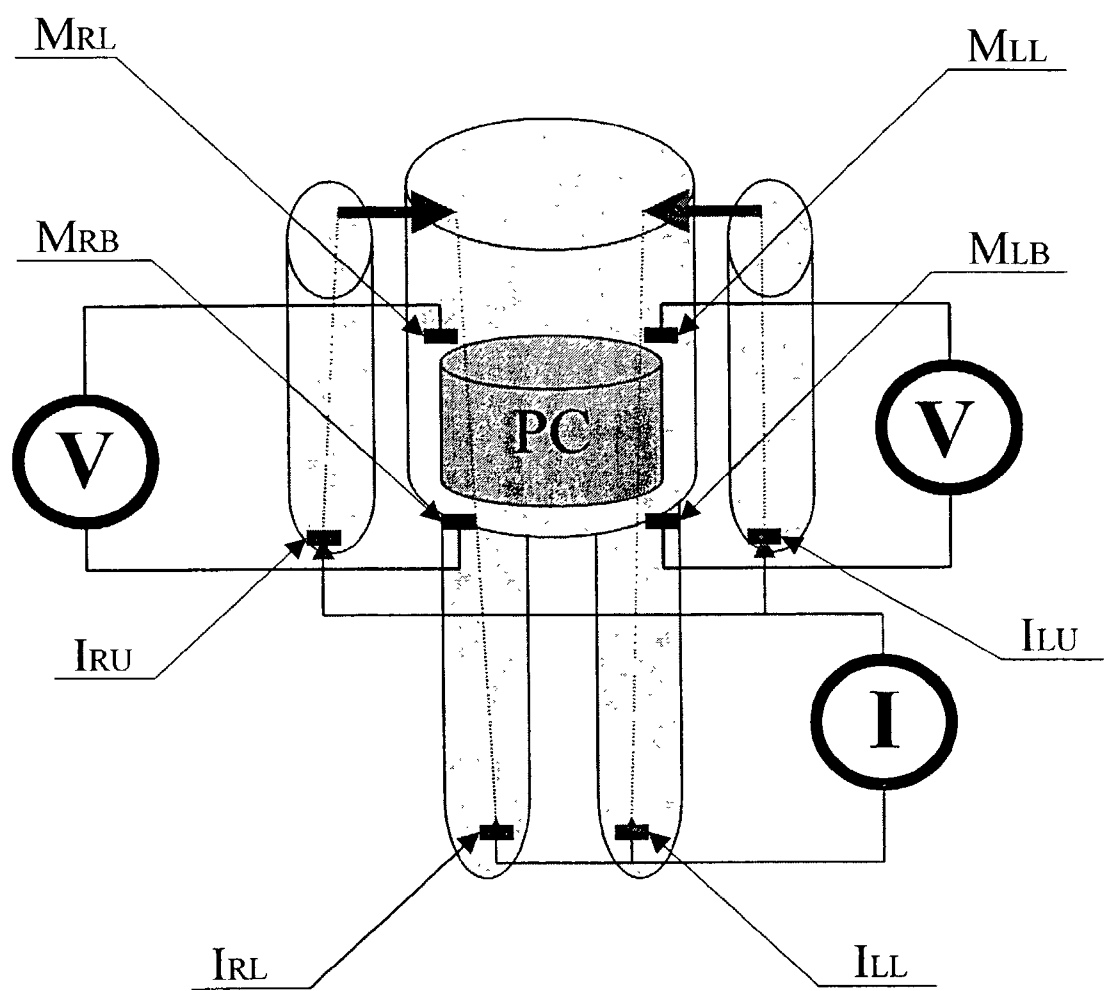
FIG. 2 is a schematic diagram illustrating suitable locations for measuring electrodes $M_{LL}$, $M_{RL}$, $M_{LB}$, and $M_{RB}$, which focus (direct) a bioimpedance measurement towards the subject's peritoneal cavity (PC).

As discussed above, the present invention relates to the measurement of the volume of fluid in the peritoneal cavity by applying current to the body of a human or an animal and recording voltages at selected portions of the body chosen to reflect the anatomical boundaries of the peritoneal cavity. FIG. 2 shows one example of the location of current-providing electrodes ($I_{RU}$, $I_{LU}$, $I_{RL}$ and $I_{LL}$) and measuring electrodes ($M_{LL}$, $M_{RL}$, $M_{LB}$, and $M_{RB}$) which achieve this result, where the peritoneal cavity (PC) is schematically shown as a shaded cylinder within the subject's torso.

The current can be applied and the voltages measured using various commercially available equipment for performing bioimpedance measurements, such as, the bioimpedance analysis devices sold by Xitron Technologies, Inc., San Diego, Calif. Generally, the use of alternating current is preferred, although direct current can be used if desired. The alternating current preferably has a frequency between about 5 kilohertz and about 500 kilohertz, a frequency of about 5 kilohertz being most preferred.

Bioimpedance analysis devices typically output both resistance and reactance values, i.e., the equipment outputs complex impedances. If desired, the reactance values and/or the magnitudes of the complex impedances can be used in the practice of the invention. However, it has been found that the real part of the impedance, i.e., the resistance value, is less sensitive to noise interference and thus its use is preferred. It should be understood, however, that the "R" values discussed above and set forth in the claims can be resistance values, reactance values, values for the magnitude of the complex impedance, or combinations thereof, as desired.

Figure 3:
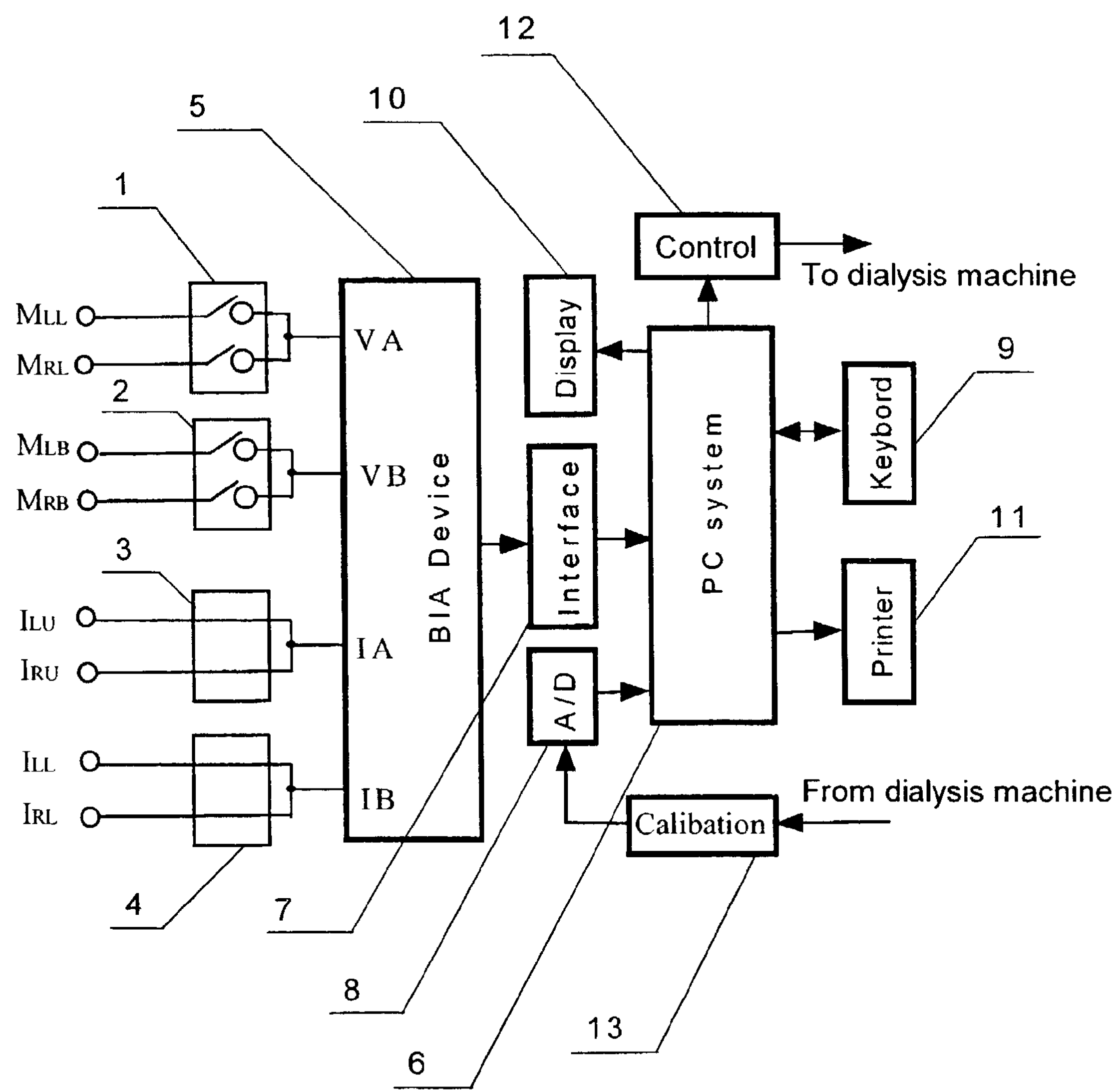
FIG. 3 is a schematic diagram of suitable equipment that can be used in the practice of the invention to apply current and to measure the resulting voltages on the surface of the subject's body.

Preferably, apparatus of the type shown in FIG. 3 is used to apply current to the current-providing electrodes and to measure sequentially the voltages at the measuring electrodes on the right and left sides of the body. As shown in FIG. 3, the apparatus includes connectors 1, 2, 3, and 4 which serve to interface bioimpedance analysis device 5 to the eight electrodes used in the practice of the invention.

It should be noted that more than eight electrodes can be used in the practice of the invention if desired, e.g., more measuring electrodes and/or more current-providing electrodes can be used. In the limit, ring or band electrodes can be used. Calculation of the average resistance R in equation (1), as well as $R_A$ and $R_B$ in equations (2) and (3), will vary when electrode configurations having more than eight electrodes and/or one or more ring electrodes are used. For example, if more than two pairs of measuring electrodes are used, the average will be over all of the vertically aligned electrode pairs. For ring electrodes used for both the loin and buttock measuring electrodes, the averaging process is performed by the electrodes themselves, so that all that is needed is a determination of the voltage between the ring electrodes while current I is applied. The approaches for other combinations (e.g., a ring electrode for the loin measuring electrode and two or more discrete electrodes for the buttock measuring electrodes) will be evident to workers skilled in the art from the disclosure herein.

Connectors 1 and 2 in FIG. 3 serve as switches to provide left and right side voltage measurements. Specifically, when these connectors are in their upper positions in FIG. 3, left side voltage differences are measured, and when they are in their lower positions, right side voltage differences are measured. Connectors 3 and 4 carry current from the bioimpedance analysis device to the upper and lower current-providing electrodes, respectively.

The output of the bioimpedance analysis device, e.g., the difference in voltage between the left measuring electrodes when connectors 1 and 2 are in their upper positions, is transmitted to personal computer 6 through a suitable interface 7. Interface 7 and/or computer 6 can perform processing, e.g., digital signal processing, on the output from bioimpedance analysis device, e.g., low pass filtering to remove noise from the voltage signal. The amount of fluid introduced or removed from the subject's peritoneal cavity during the calibration procedure is inputted to the personal computer from the dialysis equipment through A/D converter 8.

The personal computer preferably includes a keyboard 9 for entry of commands from a user and a display 10 and printer 11 for outputting data indicative of the volume of fluid in the subject's peritoneal cavity. In addition, the system preferably includes a control module 12 which provides feedback to the dialysis equipment during, for example, a continuous peritoneal dialysis procedure in order to control, for example, the ultrafiltration rate.

The current-providing electrodes need to be outboard of the measuring electrodes so as to generate a readily measurable voltage difference between the measuring electrodes. As used herein, "outboard" means that relative to the peritoneal cavity, the current-providing electrodes are more distal than the measuring electrodes.

Preferably, the current-providing electrodes and the measuring electrodes are grouped together for application to the subject's body using a common support. Such grouping facilitates use of the equipment in, for example, an in-home environment. As just one example of such a grouping, the upper current-providing electrodes and the loin measuring electrodes can be carried by a single belt which is applied to the subject just below the rib cage. Similarly, the lower current-providing electrodes and the buttock measuring electrodes can be carried by a single belt or an elastic garment which is applied to or worn by the subject. Alternatively, two belts can be used for the lower current-providing electrodes and buttock measuring electrodes, said belts being applied high on the subject's upper thigh, preferably extending up into the buttock region. As a further alternative, the current-providing and measuring electrodes can be applied using adhesive patches, e.g., two patches for the upper current-providing electrodes and loin measuring electrodes and two patches for the lower current-providing electrodes and buttock measuring electrodes. With such supports, the current-providing electrodes are preferably at least about 5 centimeters outboard of the measuring electrodes.

FIG. 6A illustrates the use of a single common support for upper current-providing electrodes ($I_{RU}$ and $I_{LU}$) and loin measuring electrodes ($M_{RL}$ and $M_{LL}$). Electrodes $I_{RU}$ and $I_{LU}$ are used to inject current from the bioimpedance analysis device to the right side and left sides of the body, respectively. Electrodes $M_{RL}$ and $M_{LL}$ are used to measure voltage from the right and left sides, respectively. Electrodes $I_{RU}$, $I_{LU}$, $M_{RL}$, and $M_{LL}$ are connected to the bioimpedance analysis device by lead 23.

The vertical distance between the two rows of electrodes is preferably about 5 cm and the width of the support is preferably about 8 cm. VELCRO fasteners 20,22 are used to close the support after it is applied to the patient's loins. Such fasteners allow the device to be used with patients having varying loin circumferences. Other types of fasteners can, of course, be used in the practice of the invention if desired.

FIGS. 6B and 6C illustrate the use of two common supports for the lower current-providing electrodes ($I_{RL}$ and $I_{LL}$) and buttock measuring electrodes ($M_{RB}$ and $M_{LB}$). These supports are placed on the patient's right and left buttocks respectively using VELCRO fasteners 20,22. The electrodes of the supports have a similar spacing to those of FIG. 6A. Likewise, the supports have a similar width. The current-providing and buttock measuring electrodes are connected to the bioimpedance analysis device by leads 24 and 25.

Both the current-providing and the measuring electrodes of FIGS. 6A, 6B, and 6C can be Ag/AgCl electrodes or can be composed of a conductive rubber which is affixed to the support.

The electrode system of FIG. 6 has the advantage that four injecting current electrodes and four measuring electrodes are integrated on three bands so that the patient does not need to place eight separate electrodes on his or her body. Further, the use of a common support leads to improved measurement accuracy because the electrodes can be more readily placed at their desired locations and are more likely to achieve a stable connection with the patient's skin.

Other arrangements can, of course, be used in the practice of the invention wherein, for example, the current-providing electrodes are significantly further outboard from the measuring electrodes, e.g., the current-providing electrodes can be placed on the subject's hands and feet as illustrated in FIG. 2.

As discussed above, current is applied simultaneously to the right and left current-providing electrodes while the left and right measurements are performed. This simultaneous current application is needed to take account of variations in the distribution of fluid within the peritoneal cavity for different subjects. Averaging of the right and left voltage measurements in calculating the volume of the peritoneal cavity is also of central importance in dealing with variations in fluid distribution in the peritoneal cavity, including changes in the distribution as a result of movement of the subject during a peritoneal dialysis procedure. It has been found that applying current on only one side, e.g., only on the side on which the voltage measurement is being made, can result in significant errors in the measurement of the volume of the peritoneal cavity for some subjects. Similarly, the use of voltage measurements from only one side of the body, rather than an average of left and right side measurements, results in a substantial loss in accuracy.

Preferably, the upper and lower current-providing electrodes (as well as the measuring electrodes) are on opposite sides of the subject's frontal plane so that current passes across that plane, although current-providing electrodes (and measuring electrodes) can be located on the same side of the frontal plane, e.g., on the subject's anterior surface, if desired.

Location of the measuring electrodes at the loin and buttock locations is also important in obtaining reliable measurements of peritoneal volumes of fluid. It has been found that locating the loin measuring electrodes substantially above or below the level of the diaphragm results in low sensitivity to changes in the peritoneal fluid volume. Similarly, locating the buttock measuring electrodes either too high or too low reduces the ability to detect the entire volume of fluid in the peritoneal cavity, especially when the subject is sitting and fluid collects at the bottom of the peritoneal cavity.

Because the distribution of peritoneal fluid varies between subjects, it is important to calibrate the voltages obtained from the measuring electrodes using a measured volume of fluid which is either inserted into the peritoneal cavity or removed therefrom. Such calibration also helps account for variations in body composition and anatomical configuration between different subjects, as well as variations in electrode placement and connection to the skin. The amount of fluid used for calibration is preferably at least one liter.

In particular, the calibration is used to determine the constant $K_P$ used in equation (1) above. Equations (1) to (3) include the effects of changes in the conductivity ($\sigma$) of the fluid in the peritoneal cavity. In a continuous peritoneal dialysis procedure such changes are very small and thus, if desired, a constant value for the conductivity can be used during calibration and measurement, e.g., a value of 21.3 mS/cm. Alternatively, the effects of changes in conductivity can be included in the calibration procedure through measurement of the conductivity of the measured volumes of fluid provided to or removed from the peritoneal cavity during calibration. Similarly, the effects of changes in conductivity during a peritoneal dialysis procedure can be taken into account by measuring the conductivity of the dialysate removed from the subject.

In certain preferred applications of the invention, the above techniques for measuring the volume of fluid in the peritoneal cavity are used to control a continuous peritoneal dialysis procedure, e.g., an overnight procedure whose duration is at least three hours and preferably at least six hours. In particular, measurements of the volume of fluid in the peritoneal cavity are made periodically or, preferably, continuously, and used to control such variables as the rate of inflow of dialysis fluid to the subject, the rate of outflow of dialysis fluid from the subject, and/or the composition of the dialysis fluid, e.g., the glucose concentration. For example, if an increase in fluid volume in the peritoneal cavity is detected, the amount of dialysis fluid supplied to the subject and/or the glucose concentration of that fluid can be decreased. The opposite changes can be made if a decrease in fluid volume is detected. In connection with these aspects of the invention, the conductivity of the fluid removed from the patient can be measured either periodically or continuously as a further measure of the course of the dialysis procedures and/or to fine tune the measurement of the volume of fluid in the peritoneal cavity, as discussed above. Various types of equipment known in the art for performing peritoneal dialysis, as well as for measuring the conductivity of fluids, can be used in the practice of these embodiments of the invention. For performing continuous peritoneal dialysis, two catheters, one for supplying dialysis fluid and the other for removing dialysate, can be used, or a single catheter having two lumens, i.e., an inflow lumen and an output lumen, can be employed.

It should be noted that in terms of clinical practice, fluid volumes in the peritoneal cavity only need to be determined to within about 0.25 liters. Accordingly, in most applications, only a single calibration needs to be performed at the beginning of a dialysis procedure, as is preferred when continuous peritoneal dialysis is performed. Of course, more frequent calibrations can be performed if desired.

The mathematical operations described herein can be performed using a variety of computers and software. For example, those operations can be performed using the VISUAL BASIC program of Microsoft's EXCEL software and a personal computer configured to run that program in accordance with the program manufacturer's specifications. The resulting programs can be stored on various storage media for use and/or distribution, e.g., the programs can be stored on removable magnetic discs, non-removable magnetic discs, or optical discs.

The overall computer system should include means for inputting data, e.g., interface 7 in FIG. 3, and means for outputting the results both in electronic and visual form, e.g., display 10 and printer 11 in FIG. 3. The output can also be stored on a disk drive, tape drive, or the like for further analysis and/or subsequent display.

Without intending to limit it in any manner, the present invention will be more fully described by the following examples. The materials and methods which are common to the examples are as follows.

Materials and Methods

Alternating current (5 kHz, 0.8 mA) was injected from alternate body sides in 1 minute intervals using four current-providing electrodes placed on both hands and feet. Four measuring electrodes were put on both sides of the loins and on the buttocks to measure impedance or, more specifically, resistance. FIG. 2 schematically shows the electrode placement that was used in collecting the data of the examples.

The subject (patient) was in a sitting body position during the measurement. The weights of drained and filling fluids were measured using an electronic scale.

Using the techniques of the invention, the volume of fluid in the peritoneal cavity was calculated from the average resistance measured on both body sides as described above. The measurements were calibrated through a determination of $K_P$ as also described above.

Switching between the right and left measurement electrodes was performed using the apparatus of FIG. 3. A XITRON bioimpedance analysis device was used to apply currents and to measure skin voltages.

Example 1

This example demonstrates that the bioimpedance techniques of the present invention reliably monitor changes in the volume of fluid in the peritoneal cavity of a subject undergoing peritoneal dialysis. It further demonstrates that the techniques of the invention reliably measure the accumulation of ultrafiltrate in the peritoneal cavity.

Four exchanges of fluid were performed on the subject. Specifically, in the first exchange, 2.3 liters of the subject's normal peritoneal fluid were drained from the subject's peritoneal cavity and replaced with 2.0 liters of dialysate. The dialysate was left in the peritoneal cavity for a dwell time of about 25 minutes, after which 1.5 liters were drained and replaced with 1.5 liters of fresh dialysate. This procedure was repeated two more times, after which 2.3 liters were drained from the peritoneal cavity and replaced with 2.0 liters of dialysate.

Figure 4:
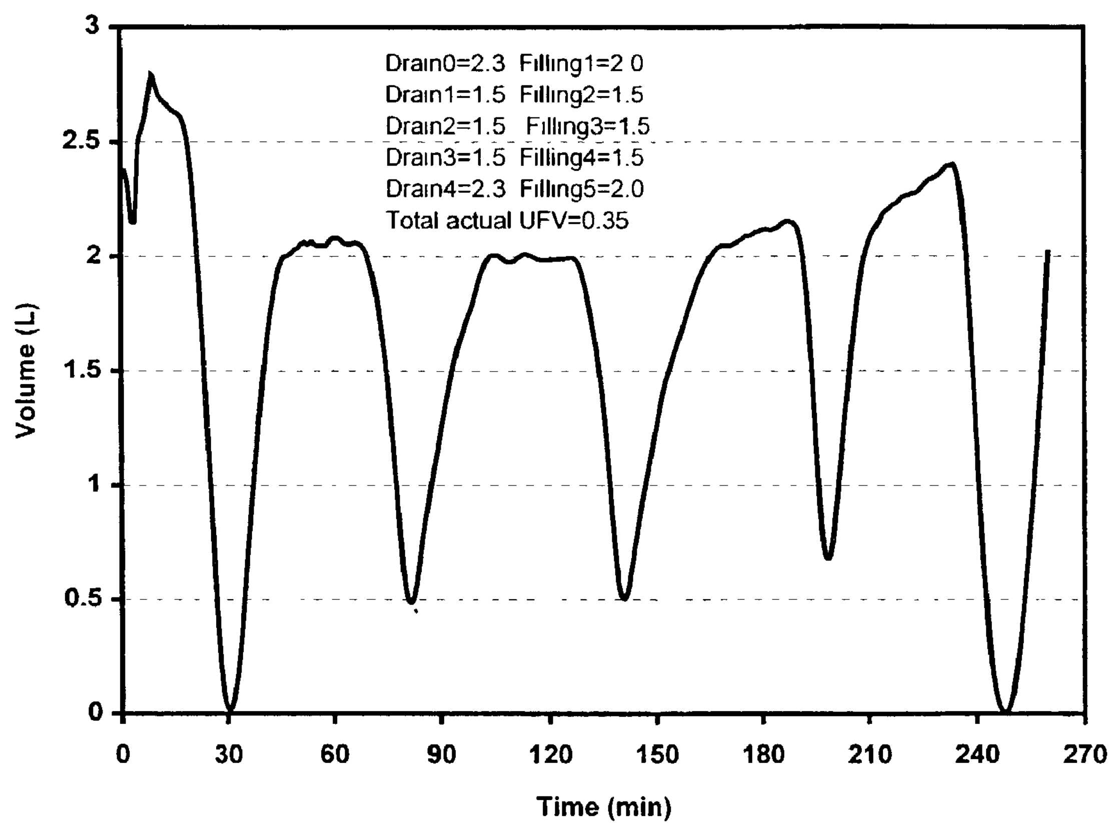
FIG. 4 illustrates use of the techniques of the invention to monitor changes in the volume of the peritoneal cavity, including the accumulation of ultrafiltrate, during a batch wise peritoneal dialysis procedure.

FIG. 4 is a trace of the volume of fluid in the peritoneal cavity calculated using equation (1) above. As can be seen in this figure, the technique of the invention accurately measured the various exchanges in peritoneal fluid. As can also be seen in FIG. 4, the technique detected the 0.35 liter ultrafiltration volume (UFV) which accumulated in the peritoneal cavity during the fourth dwell period which began at about 210 minutes into the experiment.

Example 2

This example illustrates the correlation between ultrafiltration volume (UFV) determined using equation (1) and measured UFV.

Ten subjects (patients) were used in this study, with one of the subjects being measured twice. For each subject, the normal peritoneal fluid was drained and replaced with 2 liters of dialysis fluid. After a dwell period of between 30 minutes and 2 hours, the volume of fluid in the peritoneal cavity was determined using the bioimpedance technique of the invention, i.e., equation (1) and the calibration procedures described above. The fluid in the peritoneal cavity was then removed and its volume measured. The ultrafiltration volume was defined as the difference between the volume of peritoneal fluid after the dwell period and the volume of dialysis fluid introduced at the beginning of the experiment, i.e., the difference between the final volume after the dwell period and 2 liters.

Figure 5:
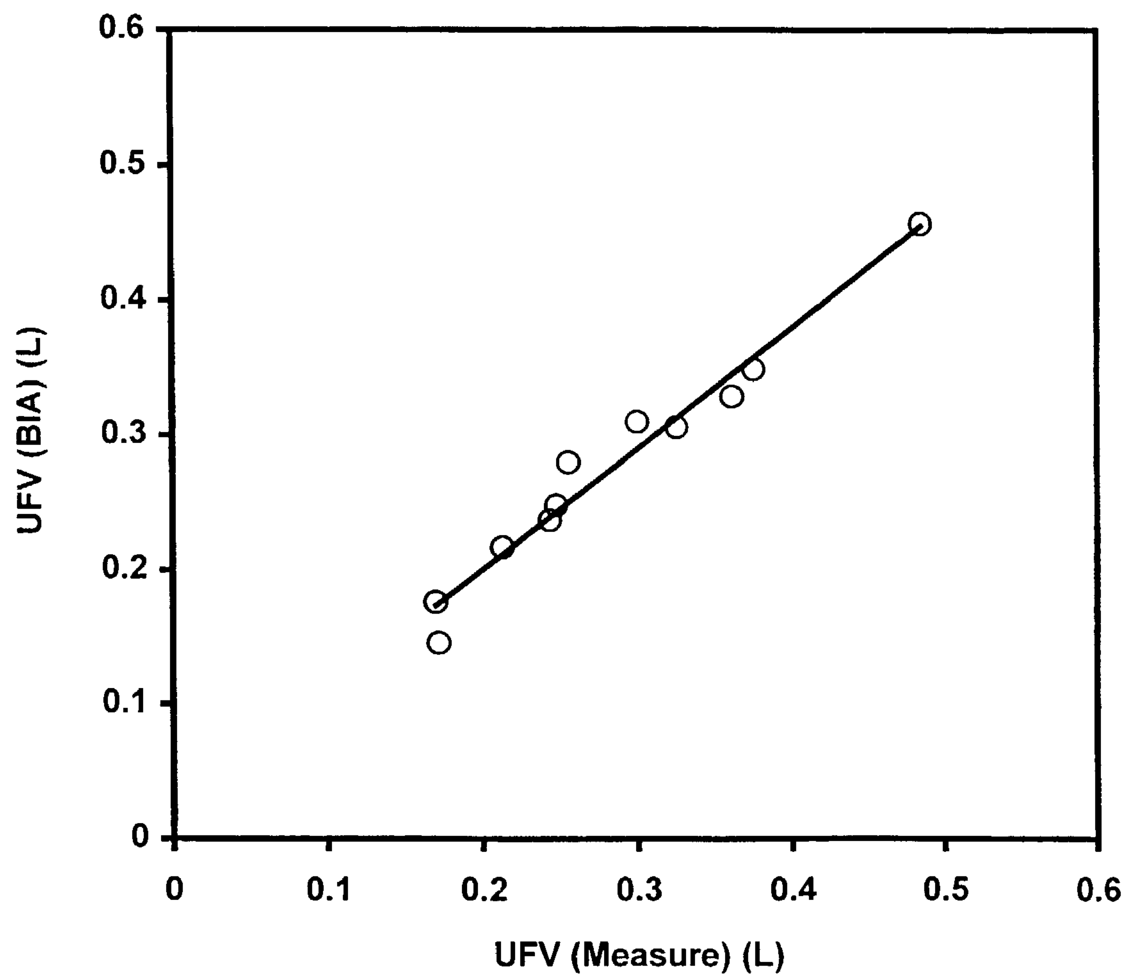
FIG. 5 shows the correlation between measured values of the ultrafiltration volume (UFV) accumulated in the peritoneal cavity (horizontal axis) and values determined using the bioimpedance analysis (BIA) techniques of the invention (vertical axis).

FIG. 5 is a plot of the results of this experiment, where the vertical axis is the ultrafiltration volume determined using equation (1) and the horizontal axis is the measured ultrafiltration volume. As can be seen in this figure, the values calculated in accordance with the technique of the invention are essentially linearly correlated with the measured values.

Example 3

This example illustrates the importance of locating the measuring electrodes in the subject's loin and buttock regions.

Twenty subjects (patients) were used in this study. For each subject, the normal peritoneal fluid was drained and replaced with dialysis fluid. The average volume of fluid drained was −2.15±0.48 liters. The average volume of dialysis fluid introduced into the peritoneal cavity was 2.1±0.2 liters. The change in fluid volume of the peritoneal cavity between the original state and the drained state (the drain volume) and between the drained stated and the filled state (fill volume) was measured using the technique of the invention with measuring electrodes placed on the subject's loins and buttocks. Measurements were also made with the measuring electrodes placed on the subject's hands and feet.

The drain and fill volumes measured using the technique of the invention were −2.0±0.5 liters and 1.7±0.45 liters, respectively. With the measuring electrodes placed on the hands and feet, the drain and fill volumes were −0.27±0.51 liters and 0.14±0.46 liters, respectively. The difference between the two measurement techniques was significant at the $P<0.001$ level. The superiority of the technique of the invention is evident from this data.

Although specific embodiments of the invention have been described and illustrated, it is to be understood that modifications can be made without departing from the invention's spirit and scope. For example, although the preferred applications of the invention are in the field of continuous peritoneal dialysis, the invention can also be used in batch wise peritoneal dialysis and in other applications in which the volume of fluid in the peritoneal cavity may be of interest, such as, in tests of peritoneal function.

A variety of other modifications which do not depart from the scope and spirit of the invention will be evident to persons of ordinary skill in the art from the disclosure herein. The following claims are intended to cover the specific embodiments set forth herein as well as such modifications, variations, and equivalents.

What is claimed is:

1. A method for determining the volume of fluid in the peritoneal cavity of a subject comprising:

(a) placing measuring electrodes $M_{LL}$ and $M_{RL}$ on the loins of the subject, $M_{LL}$ being placed on the left loin and $M_{RL}$ being placed on the right loin, $M_{LL}$ and $M_{RL}$ defining a loin plane;

(b) placing measuring electrodes $M_{LB}$ and $M_{RB}$ on the buttocks of the subject, $M_{LB}$ being placed on the left buttock and $M_{RB}$ being placed on the right buttock, $M_{LB}$ and $M_{RB}$ defining a buttock plane;

(c) placing upper current-providing electrodes $I_{LU}$ and $I_{RU}$ on the subject, $I_{LU}$ being outboard of measuring electrode $M_{LL}$ and $I_{RU}$ being outboard of measuring electrode $M_{RL}$;

(d) placing lower current-providing electrodes $I_{RL}$ and $I_{LL}$ on the subject, $I_{RL}$ being outboard of measuring electrode $M_{RB}$ and $I_{LL}$ being outboard of measuring electrode $M_{LB}$;

(e) connecting upper current-providing electrode $I_{LU}$ to upper current-providing electrode $I_{RU}$;

(f) connecting lower current-providing electrode $I_{LL}$ to lower current-providing electrode $I_{RL}$;

(g) applying current I between the connected upper current-providing electrodes and the connected lower current-providing electrodes;

(h) measuring the voltage $\Phi_L$ between $M_{LL}$ and $M_{LB}$ while current I is applied;

(i) measuring the voltage $\Phi_R$ between $M_{RL}$ and $M_{RB}$ while current I is applied; and (j) determining the volume V of fluid in the peritoneal cavity based on the equation:

$$V=(K_P/\sigma)\cdot(L_P^2/R)$$

where:

(1) $K_P$ is a subject-specific calibration constant;

(2) $\sigma$ is the conductivity of the fluid in the peritoneal cavity;

(3) $L_P$ is the distance between the loin plane and the buttock plane; and (4) R is the average of $R_L$ and $R_R$, where $$R_L=\Phi_L/I, \text{ and}$$

$$R_R=\Phi_R/I.$$

2. The method of claim 1 wherein $K_{P3}$ is determined by:

(i) performing steps (g), (h), and (i) before the introduction of a predetermined volume $V_C$ of dialysis fluid into the subject's peritoneal cavity to obtain $\Phi_{LB}$ and $\Phi_{RB}$, said dialysis fluid having a conductivity $\sigma_C$;

(ii) performing steps (g), (h), and (i) after the introduction of a predetermined volume $V_C$ of dialysis fluid into the subject's peritoneal cavity to obtain $\Phi_{LA}$ and $\Phi_{RA}$; and (iii) determining $K_P$ from the equation:

$$K_P=(\sigma_C)\cdot(V_C/L_P^2)\cdot(R_BR_A)/(R_B-R_A)$$

where $R_B=(\Phi_{LB}+\Phi_{RB})/(2I)$, and $R_A=(\Phi_{LA}+\Phi_{RA})/(2I)$.

3. The method of claim 2 where $V_C$ is at least one liter.

4. The method of claim 1 wherein $K_P$ is determined by:

(i) introducing dialysis fluid into the subject's peritoneal cavity;

(ii) performing steps (g), (h), and (i) to obtain $\Phi_{LB}$ and $\Phi_{RB}$;

(iii) removing fluid from the subject's peritoneal cavity;

(iv) performing steps (g), (h), and (i) to obtain $\Phi_{LA}$ and $\Phi_{RA}$; and (v) determining $K_P$ from the equation:

$$K_P=(\sigma_C)\cdot(V_C/L_P^2)\cdot(R_BR_A)/(R_A-R_B)$$

where $R_B=(\Phi_{LB}+\Phi_{RB})/(2I)$, $R_A=(\Phi_{LA}+\Phi_{RA})/(2I)$, and $V_C$ and $\sigma_C$ are, respectively, the volume and conductivity of the fluid removed in step (iii).

5. The method of claim 4 where $V_C$ is at least one liter.

6. The method of claim 1 wherein the current I is alternating current having a frequency in the range from about 5 kilohertz to about 500 kilohertz.

7. The method of claim 6 wherein the current I has a frequency of about 5 kilohertz.

8. The method of claim 1 wherein the upper current-providing electrodes are placed on the subject's hands and the lower current-providing electrodes are placed on the subject's feet.

9. The method of claim 1 wherein the upper current-providing electrodes are placed on the subject's trunk and the tower current-providing electrodes are placed on the subject's thighs.

10. The method of claim 1 wherein the upper current-providing electrodes and the measuring electrodes $M_{LL}$ and $M_{RL}$ are carried by a common support which is placed on the subject's trunk.

11. The method of claim 1 wherein the lower current-providing electrode $I_{LL}$ and the measuring electrode $M_{LB}$ are carried by a first common support which is placed at least in part on the subject's left leg and the lower current-providing electrode $I_{RL}$ and the measuring electrode $M_{RB}$ are carried by a second common support which is placed at least in part on the subjects right leg.

12. A method of controlling a peritoneal dialysis procedure comprising:

(A) continuously flowing dialysis fluid through a subject's peritoneal cavity;

(B) while step (A) is being performed, determining the volume of fluid in the peritoneal cavity by a bioimpedance measurement directed at the peritoneal cavity; and (C) controlling step (A) based on the volume of fluid in the peritoneal cavity determined in step (B).

13. The method of claim 12 wherein step (B) is performed by:

(a) placing measuring electrodes $M_{LL}$ and $M_{RL}$ on the loins of the subject, $M_{LL}$ being placed on the left loin and $M_{RL}$ being placed on the right loin, $M_{LL}$ and $M_{RL}$ defining a loin plane;

(b) placing measuring electrodes $M_{LB}$ and $M_{RB}$ on the buttocks of the subject, $M_{LB}$ being placed on the left buttock and $M_{RB}$ being placed on the right buttock, $M_{LB}$ and $M_{RB}$ defining a buttock plane;

(c) placing upper current-providing electrodes $I_{LU}$ and $I_{RU}$ on the subject, $I_{LU}$ being outboard of measuring electrode $M_{LL}$ and $I_{RU}$ being outboard of measuring electrode $M_{RL}$;

(d) placing lower current-providing electrodes $I_{RL}$ and $I_{LL}$ on the subject, $I_{RL}$ being outboard of measuring electrode $M_{RB}$ and $I_{LL}$ being outboard of measuring electrode $M_{LB}$;

(e) connecting upper current-providing electrode $I_{LU}$ to upper current-providing electrode $I_{RU}$;

(f) connecting lower current-providing electrode $I_{LL}$ to lower current-providing electrode $I_{RL}$;

(g) applying current I between the connected upper current-providing electrodes and the connected lower current-providing electrodes;

(h) measuring the voltage $\Phi_L$ between $M_{LL}$ and $M_{LB}$ while current I is applied;

(i) measuring the voltage $\Phi_R$ between $M_{RL}$ and $M_{RB}$ while current I is applied; and (j) determining the volume V of fluid in the peritoneal cavity based on the equation:

$$V=(K_P/\sigma)\cdot(L_P^2/R)$$

where:

(1) $K_P$ is a subject specific calibration constant;

(2) $\sigma$ is the conductivity of the fluid in the peritoneal cavity;

(3) $L_P$ is the distance between the loin plane and the buttock plane; and (4) R is the average of $R_L$ and $R_R$, where $$R_L=\Phi_L/I, \text{ and}$$

$$R_R=\Phi_R/I.$$

14. The method of claim 12 where the rate of flow of dialysis fluid into, out of, or both into and out of the peritoneal cavity is controlled in step (C).

15. The method of claim 12 where the composition of the dialysis fluid is controlled in step (C).

16. The method of claim 12 including the additional step of determining the conductivity of dialysis fluid removed from the subject while step (A) is being performed.

17. The method of claim 12 wherein in step (A), the continuous flowing of dialysis fluid through the subject's peritoneal cavity is performed for a period of at least three hours and step (B) is performed at least at regular intervals throughout said period.

18. The method of claim 17 wherein step (B) is performed substantially continuously throughout said period.

19. The method of claim 12 wherein in step (A), the continuous flowing of dialysis fluid through the subject's peritoneal cavity is performed for a period of at least six hours and step (B) is performed at least at regular intervals throughout said period.

20. The method of claim 19 wherein step (B) is performed substantially continuously throughout said period.

21. The method of claim 12 wherein in step (B), the bioimpedance measurement employs measuring electrodes located in the subject's loin and buttock regions.

22. Apparatus for determining the volume of fluid in the peritoneal cavity of a subject comprising:

(a) measuring electrodes $M_{LL}$ and $M_{RL}$ for placement on the loins of the subject, $M_{LL}$ to be placed on the left loin and $M_{RL}$ to be placed on the right loin such that, when so placed, $M_{LL}$ and $M_{RL}$ define a loin plane;

(b) measuring electrodes $M_{LB}$ and $M_{RB}$ for placement on the buttocks of the subject, $M_{LB}$ to be placed on the left buttock and $M_{RB}$ to be placed on the right buttock such that, when so placed, $M_{LB}$ and $M_{RB}$ define a buttock plane;

(c) upper current-providing electrodes $I_{LU}$ and $I_{RU}$ for placement on the subject;

(d) lower current-providing electrodes $I_{RL}$ and $I_{LL}$ for placement on the subject;

(e) means for connecting upper current-providing electrode $I_{LU}$ to upper current-providing electrode $I_{RU}$;

(f) means for connecting lower current-providing electrode $I_{LL}$ to lower current-providing electrode $I_{RL}$;

(g) means for applying a current I between the connected upper current-providing electrodes and the connected lower current-providing electrodes;

(h) means for measuring the voltage $\Phi_L$ between $M_{LL}$ and $M_{LB}$ while current I is applied;

(i) means for measuring the voltage $\Phi_R$ between $M_{RL}$ and $M_{RB}$ while current I is applied; and (j) means for determining the volume V of fluid in the peritoneal cavity based on the equation:

$$V=(K_P/\sigma)\cdot(L_P^2/R)$$

where:

(1) $K_P$ is a subject-specific calibration constant;

(2) σ is the conductivity of the fluid in the peritoneal cavity;

(3) $L_P$ is the distance between the loin plane and the buttock plane; and (4) R is the average of $R_L$ and $R_R$, where $R_L=\Phi_L/I$, and $R_R=\Phi_R/I$.

23. The apparatus of claim 22 further comprising means for determining $K_P$, said means comprising:

(i) means for determining the voltage $\Phi_{LB}$ between $M_{LL}$ and $M_{LB}$ and the voltage $\Phi_{RB}$ between $M_{RL}$ and $M_{RB}$ while current I is applied, said determination being made before the introduction of a predetermined volume $V_C$ of dialysis fluid into the subject's peritoneal cavity, said dialysis fluid having a conductivity ac;

(ii) means for determining the voltage $\Phi_{LA}$ between $M_{LL}$ and $M_{LB}$ and the voltage $\Phi_{RA}$ between $M_{RL}$ and $M_{RB}$ while current I is applied, said determination being made after the introduction of a predetermined volume $V_C$ of dialysis fluid into the subject's peritoneal cavity; and (iii) means for determining $K_P$ from the equation:

$$K_P=(\sigma_C)\cdot(V_C/L_P^2)\cdot(R_BR_A)/(R_B-R_A)$$

where $R_B=(\Phi_{LB}+\Phi_{RB})/(2I)$, and $R_A=(\Phi_{LA}+\Phi_{RA})/(2I)$.

24. The apparatus of claim 22 further comprising means for determining $K_P$, said means comprising:

(i) means for introducing dialysis fluid into the subject's peritoneal cavity;

(ii) means for determining the voltage $\Phi_{LB}$ between $M_{LL}$ and $M_{LB}$ and the voltage $\Phi_{RB}$ between $M_{RL}$ and $M_{RB}$ while current I is applied, said determination being made before removal of fluid from the subject's peritoneal cavity;

(iii) means for removing fluid from the subject's peritoneal cavity;

(iv) means for measuring the volume $V_C$ of fluid removed from the subject's peritoneal cavity;

(v) means for determining the voltage $\Phi_{LA}$ between $M_{LL}$ and $M_{LB}$ and the voltage $\Phi_{RA}$ between $M_{RL}$ and $M_{RB}$ while current I is applied, said determination being made after the removal of the volume $V_C$ of fluid from the subject's peritoneal cavity; and (vi) means for determining $K_P$ from the equation:

$$K_P=(\sigma_C)\cdot(V_C/L_P^2)\cdot(R_BR_A)/(R_A-R_B)$$

where $$R_B=(\Phi_{LB}+\Phi_{RB})/(2I),$$

$$R_A=(\Phi_{LA}+\Phi_{RA})/(2I),\text{ and}$$

$\sigma_C$ is the conductivity of the fluid removed from the subject's peritoneal cavity.

25. The apparatus of claim 22 wherein the current I is alternating current having a frequency in the range from about 5 kilohertz to about 500 kilohertz.

26. The apparatus of claim 25 wherein the current I has a frequency of about 5 kilohertz.

27. The apparatus of claim 22 further comprising a support for carrying the upper current-providing electrodes and the measuring electrodes $M_{LL}$ and $M_{RL}$.

28. The apparatus of claim 22 further comprising a first support for carrying the lower current-providing electrode $I_{LL}$ and the measuring electrode $M_{LB}$ and a second support for carrying the lower current-providing electrode $I_{RL}$ and the measuring electrode $M_{RB}$.

29. Apparatus for performing a peritoneal dialysis procedure comprising:

(A) first means for continuously flowing dialysis fluid through a subject's peritoneal cavity, said flowing of dialysis fluid being capable of causing the accumulation of ultrafiltrate from the subject in the peritoneal cavity;

(B) second means for determining the volume of fluid in the peritoneal cavity while dialysis fluid is flowed through the subject's peritoneal cavity, said second means comprising means for performing a bioimpedance measurement directed at the peritoneal cavity; and (C) third means for controlling the first means based on the volume of fluid in the peritoneal cavity determined by the second means.

30. The apparatus of claim 29 wherein the means for performing a bioimpedance measurement directed at the peritoneal cavity comprises:

(a) measuring electrodes $M_{LL}$ and $M_{RL}$ for placement on the loins of the subject, $M_{LL}$ to be placed on the left loin and $M_{RL}$ to be placed on the right loin such that, when so placed, $M_{LL}$ and $M_{RL}$ define a loin plane;

(b) measuring electrodes $M_{LB}$ and $M_{RB}$ for placement on the buttocks of the subject, $M_{LB}$ to be placed on the left buttock and $M_{RB}$ to be placed on the right buttock such that, when so placed, $M_{LB}$ and $M_{RB}$ define a buttock plane;

(c) upper current-providing electrodes $I_{LU}$ and $I_{RU}$ for placement on the subject;

(d) lower current-providing electrodes $I_{RL}$ and $I_{LL}$ for placement on the subject;

(e) means for connecting upper current-providing electrode $I_{LU}$ to upper current-providing electrode $I_{RU}$;

(f) means for connecting lower current-providing electrode $I_{LL}$ to lower current-providing electrode $I_{RL}$;

(g) means for applying a current I between the connected upper current-providing electrodes and the connected lower current-providing electrodes;

(h) means for measuring the voltage $\Phi_L$ between $M_{LL}$ and $M_{LB}$ while current I is applied;

(i) means for measuring the voltage $\Phi_R$ between $M_{RL}$ and $M_{RB}$ while current I is applied; and (j) means for determining the volume V of fluid in the peritoneal cavity based on the equation:

$$V=(K_P/\sigma)\cdot(L_P^2/R)$$

where:

(1) $K_P$ is a subject-specific calibration constant;

(2) $\sigma$ is the conductivity of the fluid in the peritoneal cavity;

(3) $L_P$ is the distance between the loin plane and the buttock plane; and (4) R is the average of $R_L$ and $R_R$, where $$R_L=\Phi_L/I, \text{ and}$$

$$R_R=\Phi_R/I.$$

31. The apparatus of claim 29 wherein the third means controls the ultrafiltration rate of the first means.

32. The apparatus of claim 29 wherein the third means controls the rate at which the first means flows dialysis fluid through the subject's peritoneal cavity.

33. The apparatus of claim 29 wherein the third means controls the composition of the dialysis fluid which the first means flows through the subject's peritoneal cavity.

34. The apparatus of claim 29 wherein the third means includes means for determining the conductivity of the dialysis fluid removed from the subject by the first means.

35. An article of manufacture comprising a computer usable medium having computer readable code means embodied therein for:

(a) determining the volume V of fluid in the peritoneal cavity of a subject based on the equation:

$$V=(K_P/\sigma)\cdot(L_P^2/R)$$

where:

(1) $K_P$ is a subject-specific calibration constant (2) $\sigma$ is the conductivity of the fluid in the peritoneal cavity:

(3) $L_P$ is the distance between a loin plane and a buttock plane of the subject, the loin plane being established by the locations of measuring electrodes $M_{LL}$ and $M_{RL}$ placed on the subject's left and right loins, respectively, and the buttock plane being established by measuring electrodes $M_{LB}$ and $M_{RB}$ placed on the subject's left and right buttocks, respectively; and (4) R is the average of $R_L$ and $R_R$, where (i) $R_L=\Phi_L/I$, (ii) $R_R=\Phi_R/I$, and (iii) I is an applied current between connected upper current-providing electrodes $I_{LU}$ $I_{RU}$ and connected lower current-providing electrodes $I_{RL}$ and $I_{LL}$ placed on the subject with $I_{LU}$ and $I_{RU}$ being outboard of measuring electrode $M_{LL}$, $I_{RU}$ being outboard of measuring electrode $M_{RL}$, $I_{RL}$ being outboard of measuring electrode $M_{RB}$ and $I_{LL}$ being outboard of measuring electrode $M_{LB}$, and (iv) $\Phi_L$ and $\Phi_R$ are measured voltages between $M_{LL}$ and $M_{LB}$ and between $M_{RL}$ and $M_{RB}$, respectively, while current I is applied; and (b) displaying the value of the calculated volume V to the subject and/or to a care provider and/or controlling the flow of dialysis fluid through the suibject's peritoneal cavity using the calculated volume V.

36. An article of manufacture comprising a computer usable medium having computer readable code means embodied therein for:

(a) determining a subject-specific for use in determining the volume of fluid in the subject's peritoneal cavity calibration constant $K_P$ from the equation:

$$K_P=(\sigma_C)\cdot(V_C/L_P^2)\cdot(R_BR_A)/(R_B-R_A)$$

where (i) $R_B=(\Phi_{LB}+\Phi_{RB})/(2I)$;

(ii) $R_A=(\Phi_{LA}+\Phi_{RA})/(2I)$;

(iii) $V_C$ and $\sigma_C$ are, respectively, the volume and conductivity of a predetermined volume of dialysis fluid;

(iv) $L_P$ is the distance between a loin plane and a buttock plane of the subject, the loin plane being established by the locations of measuring electrodes $M_{LL}$ and $M_{RL}$ placed on the subject's left and right loins, respectively, and the buttock plane being established by measuring electrodes $M_{LB}$ and $M_{RB}$ placed on the subject's left and right buttocks, respectively;

(v) I is an applied current between connected upper current-providing electrodes $I_{LU}$ and $I_{RU}$ connected lower current-providing electrodes $I_{RL}$ and $I_{LL}$ placed on the subject with $I_{LU}$ being outboard of measuring electrode $M_{LL}$, $I_{RU}$ being outboard of measuring electrode $M_{RL}$, $I_{RL}$ being outboard of measuring electrode $M_{RB}$ and $I_{LL}$ being outboard of measuring electrode $M_{LB}$, (vi) $\Phi_{LA}$ and $\Phi_{RA}$ are measured voltages between $M_{LL}$ and $M_{LB}$ and between $M_{RL}$ and $M_{RB}$, respectively, obtained before introduction of the predetermined volume of dialysis fluid into the subject's peritoneal cavity and while current I is applied; and (vii) $\Phi_{LA}$ and $\Phi_{RA}$ are measured voltages between $M_{LL}$ and $M_{LB}$ and between $M_{RL}$ and $M_{RB}$, respectively, obtained after introduction of the predetermined volume of dialysis fluid into the subject's peritoneal cavity and while current I is applied; and (b) displaying the value of the calculated subject-specific calibration constant $K_P$ to the subject and/or to a care provider and/or controlling the flow of dialysis fluid through the subject's peritoneal cavity using the calculated subject-specific calibration constant $K_P$.

37. An article of manufacture comprising a computer usable medium having computer readable code means embodied therein for:

(a) determining a subject-specific for use in determining the volume of fluid in the subject's peritoneal cavity calibration constant $K_P$ from the equation:

$$K_P=(\sigma_C)\cdot(V_C/L_P^2)\cdot(R_BR_A)/(R_B-R_A)$$

where (i) $R_B=(\Phi_{LB}+\Phi_{RB})/(2I)$;

(ii) $R_A=(\Phi_{LA}+\Phi_{RA})/(2I)$;

(iii) $L_P$ is the distance between a loin plane and a buttock plane of the subject, the loin plane being established by the locations of measuring electrodes $M_{LL}$ and $M_{RL}$ placed on the subject's left and right loins, respectively, and the buttock plane being established by measuring electrodes $M_{LB}$ and $M_{RB}$ placed on the subject's left and right buttocks, respectively;

(iv) I is an applied current between connected upper current-providing electrodes $I_{LU}$ and $I_{RU}$ and connected lower current-providing electrodes $I_{RL}$ and $I_{LL}$ placed on the subject with $I_{LU}$ being outboard of measuring electrode $M_{LL}$, $I_{RU}$ being outboard of measuring electrode $M_{RL}$, $I_{RL}$ being outboard of measuring electrode $M_{RB}$ and $I_{LL}$ being outboard of measuring electrode $M_{LB}$, (v) $\Phi_{LB}$ and $\Phi_{RB}$ are measured voltages between $M_{LL}$ and $M_{LB}$ and between $M_{RL}$ and $M_{RB}$, respectively, obtained after introduction of dialysis fluid into the subject's peritoneal cavity and while current I is applied:

(vi) $\Phi_{LA}$ and $\Phi_{RA}$ are measured voltages between $M_{LL}$ and $M_{LB}$ and between $M_{RL}$ and $M_{RB}$, respectively, obtained after removal of fluid from the subject's peritoneal cavity and while current I is applied; and (vii) $V_C$ and $\sigma_C$ are, respectively, the volume and conductivity of the fluid removed from the subject's peritoneal cavity; and (b) displaying the value of the calculated subject-specific calibration constant $K_P$ to the subject and/or to a care provider and/or controlling the flow of dialysis fluid through the subject's peritoneal cavity using the calculated subject-specific calibration constant $K_P$.

38. Apparatus comprising a computer which has been programmed to:

(a) determine the volume V of fluid in the peritoneal cavity of a subject based on the equation:

$$V=(K_P/\sigma)\cdot(L_P^2/R)$$

where:

(1) $K_P$ is a subject-specific calibration constant, (2) $\sigma$ is the conductivity of the fluid in the peritoneal cavity:

(3) $L_P$ is the distance between a loin plane and a buttock plane of the subject, the loin plane being established by the locations of measuring electrodes $M_{LL}$, and $M_{RL}$, placed on the subject's left and right loins, respectively, and the buttock plane being established by measuring electrodes $M_{LB}$ and $M_{RB}$ placed on the subject's left and right buttocks, respectively; and (4) R is the average of $R_L$ and $R_R$, where (i) $R_L=\Phi_L/I$, (ii) $R_R=\Phi_R/I$, and (iii) I is an applied current between connected upper current-providing electrodes $I_{LU}$ and $I_{RU}$ and connected lower current-providing electrodes $I_{RL}$ and $I_{LL}$ placed on the subject with $I_{LU}$ being outboard of measuring electrode $M_{LL}$, $I_{RU}$ being outboard of measuring electrode $M_{RL}$, $I_{RL}$ being outboard of measuring electrode $M_{RB}$ and $I_{LL}$ being outboard of measuring electrode $M_{LB}$, and (iv) $\Phi_L$ and $\Phi_R$ are measured voltages between $M_{LL}$ and $M_{LB}$ and between $M_{RL}$ and $M_{RB}$, respectively, while current I is applied; and (b) display the value of the calculated volume V to the subject and/or to a care provider and/or control the flow of dialysis fluid through the subject's peritoneal cavity using the calculated volume V.

39. Apparatus comprising a computer which has been programmed to:

(a) determine a subject-specific for use in determining the volume of fluid in the subject's peritoneal cavity calibration constant $K_P$ from the equation:

$$K_P=(\sigma_C)\cdot(V_C/L_P^2)\cdot(R_BR_A)/(R_B-R_A)$$

where (i) $R_B=(\Phi_{LB}+\Phi_{RB})/(2I)$;

(ii) $R_A=(\Phi_{LA}+\Phi_{RA})/(2I)$;

(iii) $V_C$ and $\sigma_C$ are, respectively, the volume and conductivity of a predetermined volume of dialysis fluid;

(iv) $L_P$ is the distance between a loin plane and a buttock plane of the subject, the loin plane being established by the locations of measuring electrodes $M_{LL}$ and $M_{RL}$ placed on the subject's left and right loins, respectively, and the buttock plane being established by measuring electrodes $M_{LB}$ and $M_{RB}$ placed on the subject's left and right buttocks, respectively;

(v) I is an applied current between connected upper current-providing electrodes $I_{LU}$ a $I_{RU}$ and connected lower current-providing electrodes $I_{RL}$ and $I_{LL}$ placed on the subject with $I_{LU}$ being outboard of measuring electrode $M_{LL}$, $I_{RU}$ being outboard of measuring electrode $M_{RL}$, $I_{RL}$ being outboard of measuring electrode $M_{RB}$ and $I_{LL}$ being outboard of measuring electrode $M_{LB}$, (vi) $\Phi_{LB}$ and $\Phi_{RB}$ are measured voltages between $M_{LL}$ and $M_{LB}$ and between $M_{RL}$ and $M_{RB}$, respectively, obtained before introduction of the predetermined volume of dialysis fluid into the subject's peritoneal cavity and while current I is applied; and (vii) $\Phi_{LA}$ and $\Phi_{RA}$ are measured voltages between $M_{LL}$ and $M_{LB}$ and between $M_{RL}$ and $M_{RB}$, respectively, obtained after introduction of the predetermined volume of dialysis fluid into the subject's peritoneal cavity and while current I is applied; and (b) display the value of the calculated subject-specific calibration constant $K_P$ to the subject and/or to a care provider and/or control the flow of dialysis fluid through the subject's peritoneal cavity using the calculated subject-specific calibration constant $K_P$.

40. Apparatus comprising a computer which has been programmed to:

(a) determine a subject-specific for use in determining the volume of fluid in the subject's peritoneal cavity calibration constant $K_P$ from the equation:

$$K_P=(\sigma_C)\cdot(V_C/L_P^2)\cdot(R_BR_A)/(R_B-R_A)$$

where (i) $R_B=(\Phi_{LB}+\Phi_{RB})/(2I)$;

(ii) $R_A=(\Phi_{LA}+\Phi_{RA})/(2I)$;

(iii) $L_P$ is the distance between a loin plane and a buttock plane of the subject, the loin plane being established by the locations of measuring electrodes $M_{LL}$ and $M_{RL}$ placed on the subject's left and right loins, respectively, and the buttock plane being established by measuring electrodes $M_{LB}$ and $M_{RB}$ placed on the subject's left and right buttocks, respectively (iv) I is an applied current between connected upper current-providing electrodes $I_{LU}$ and $I_{RU}$ and connected lower current-providing electrodes $I_{RL}$ and $I_{LL}$ placed on the subject with $I_{LU}$ being outboard of measuring electrode $M_{LL}$, $I_{RU}$ being outboard of measuring electrode $M_{RL}$, $I_{RL}$ being outboard of measuring electrode $M_{RB}$ and $I_{LL}$ being outboard of measuring electrode $M_{LB}$, (v) $\Phi_{LB}$ and $\Phi_{RB}$ are measured voltages between $M_{LL}$ and $M_{LB}$ and between $M_{RL}$ and $M_{RB}$, respectively, obtained after introduction of dialysis fluid into the subject's peritoneal cavity and while current I is applied;

(vi) $\Phi_{LA}$ and $\Phi_{RA}$ are measured voltages between $M_{LL}$ and $M_{LB}$ and between $M_{RL}$ and $M_{RB}$, respectively, obtained after removal of fluid from the subject's peritoneal cavity and while current I is applied; and (vii) $V_C$ and $\sigma_C$ are, respectively, the volume and conductivity of the fluid removed from the subject's peritoneal cavity; and (b) display the value of the calculated subject-specific calibration constant $K_P$ to the subject and/or to a care provider and/or control the flow of dialysis fluid through the subject's peritoneal cavity using the calculated subject-specific calibration constant $K_P$.

* * * * *